United States Patent [19]
Koike et al.

[11] Patent Number: 6,056,760
[45] Date of Patent: May 2, 2000

[54] DEVICE FOR INTRACARDIAC SUTURE

[75] Inventors: Kazuyuki Koike, Tokyo-to; Yoshikazu Kishigami; Katsuya Miyagawa, both of Osaka, all of Japan

[73] Assignee: Nissho Corporation, Osaka-fu, Japan

[21] Appl. No.: 09/016,635

[22] Filed: Jan. 30, 1998

[30] Foreign Application Priority Data

Jan. 30, 1997 [JP] Japan .................................... 9-016301

[51] Int. Cl.[7] .................................................. A61B 17/04
[52] U.S. Cl. ........................... 606/148; 606/144; 606/139
[58] Field of Search .................................... 606/232, 139, 606/148, 144

[56] References Cited

U.S. PATENT DOCUMENTS

| | | | |
|---|---|---|---|
| 3,874,388 | 4/1975 | King et al. | 128/334 |
| 4,235,238 | 11/1980 | Ogiu et al. | 128/334 |
| 4,741,330 | 5/1988 | Hayhurst | 128/92 YF |
| 5,282,827 | 2/1994 | Kensey et al. | 606/215 |
| 5,425,744 | 6/1995 | Fagan et al. | 606/213 |
| 5,470,337 | 11/1995 | Moss | 606/139 |
| 5,647,874 | 7/1997 | Hayhurst | 606/72 |
| 5,810,848 | 9/1998 | Hayhurst | 606/144 |

FOREIGN PATENT DOCUMENTS

| | | |
|---|---|---|
| 0 500 215 A1 | 8/1992 | European Pat. Off. . |
| 0 769 272 A1 | 4/1997 | European Pat. Off. . |

Primary Examiner—Gary Jackson
Attorney, Agent, or Firm—Kubovcik & Kubovcik

[57] ABSTRACT

Disclosed is a device for intracardiac suture. The device includes a rod 3 provided with a grip member 31 at a proximal end thereof and having a flexible end portion; a piercing catheter 2 having a lumen 21 for movably holding the rod 3 and a flexible distal end portion with a piercing needle 25 at a distal end thereof, and provided with a hemostatic means 24 at a proximal end thereof; a sheath 1 having a lumen 11 for movably holding the piercing catheter 2 and provided with a hemostatic means 14 at a proximal end thereof; and an engaging member 4 which can be accommodated in the lumen 21 of the piercing catheter 2 and to which a suture can be fitted; wherein the engaging member 4 when accommodated in the piercing catheter 2 can be pushed out of the piercing catheter 2 by pushing said rod 3. The device is applicable to intracardiac suture for various configurations of ASD.

4 Claims, 10 Drawing Sheets

DEVICE FOR INTRACARDIAC SUTURE

FIELD OF THE INVENTION

The present invention relates to a device for intracardiac suture and, more particularly, to a device for an intracardiac suture procedure suitable for a surgical technique, a so-called transcatheter atrioseptopexy, in which a sewing device is inserted into a peripheral blood vessel and manipulated into the heart by cardiocatheterization under cross-sectional echocardiography to sew an atrial septal defect (ASD) by direct suturing.

BACKGROUND OF THE INVENTION

In general, congenital cardiac diseases such as ASD have been treated by a surgical operation. As a matter of course, such a surgical operation includes not only treatment of the affected part but also thoracotomy or laparotomy and causes significant damage to a patient. In particular, it causes serious damage to child patients who are poor in physical strength.

Recently, a non-operative method for occlusion of atrial septal defects has been developed, in which a cardiocatheter is transvascularly inserted into the heart. This method is known as a percutaneous transluminal therapeutic catheterization, and the first clinical success in this method was reported in 1976 by King and Mill. In the method of King et al, an atrial septal defect is closed by introducing a pair of umbrella-like members for the left atrium and the right atrium into the atria with an insertion tool composed of a double-layered catheter and a core wire coaxially arranged therein, placing the members on the opposite sides of the defect, and locking them together at a central hub which crosses the defect.

However, this method requires the use of a very large-sized insertion tool and hard umbrella-like members, thus making it impossible to apply it to children, especially to preschool children. For this reason, as a result of efforts to miniaturize such a device, Rashkind developed a single-umbrella type plug having a hook and succeeded in clinical application of the device to a child in 1977. However, this method has a defect that the plug is sometimes hooked on an unintended side of the heart because of being provided with the hook. Once the umbrella-like member is opened, it is impossible to change the hooked position as well as to draw back the device from the heart. This requires an emergency surgical operation when the plug is hooked on an unintended side of the heart. In order to overcome such disadvantages, Rashkind further developed a plug comprising two umbrella-shaped occluders having eight stainless steel struts and being connectable to each other. The device has been put into clinical use widely for occlusion of patient ductus arteriosus.

Japanese unexamined patent application No. 5-237128 filed by James E. Lock et al. discloses an interatrial occlusion device comprising two umbrella-shaped members composed of eight stainless steel struts as in Rashkind's device, each strut being provided at a central part thereof with a spring coil. This device is firmly fixed to the thin interatrial septum by closely adhering the two umbrella-shaped members to each other in an overlapping state. This device is called a clam shell-shaped interatrial occluder because of its configuration similar to that of a clam being a bivalve. The procedure is carried out by inserting an elongated sheath with a thickness of 11 French through the femoral vein. This device has been widely used for closing atrial septal defects by means of percutaneous transluminal therapeutic catheterization since the device can be applied to patients with a weight of 8 kg and above.

However, there is a limitation to the application of these occlusion plugs since only occlusion plugs with a uniform shape are prepared for various configurations of atrial septal defects and since the occlusion of a defective opening or hole requires use of an occlusion plug twice the size of the defective opening or hole. These devices therefore, can be applied only to relatively small defective openings or holes present in the central part of the atrioventricular septum. In addition, there is a fear of bad effects due to use of occlusion plugs since there is no data on long-term use of occlusion plugs left in the heart.

The present inventors have already proposed a catheter assembly for intracardiac suture, which is applicable to various configurations of ASD and can percutaneously sew and close ASD, as disclosed in Japanese unexamined patent application No. 7-171173. This catheter assembly comprises a piercing member and a tabular member. Using this catheter assembly, the piercing member is placed at the edge of the defective opening or hole in the heart, and the defective opening or hole is closed by the tabular member.

This catheter assembly is advantageous in that it is applicable to various configurations of ASD, but is disadvantageous for the following reasons. In the method using this catheter assembly, since a piercing member having a sharp edge at a distal end is pierced into the edge of the defective opening or hole in the heart and since the tabular member is left in the heart for a long period of time to close the defective opening or hole, the method will be accompanied by some postoperative problems. In addition, since the tabular member must be large so that it can close the defective opening or hole, a large foreign substance is left in the body after the operation. For these reasons, further improvements in the catheter assembly to improve its safety have been desired.

SUMMARY OF THE INVENTION

It is, therefore, an object of the present invention to provide a catheter assembly for intracardiac suture operation, which is suitable for various configurations of ASD, can be handled with ease and can securely sew and close a defective opening or hole.

As a result of assiduous studies for solving the problems in the prior art, the present inventors developed a technical idea of employing an engaging member or means capable of being engaged with ASD and functioning as a fixation end for a suture to close the ASD. Based on this technical idea, the present invention was completed.

According to the present invention, the above object is achieved by providing a device for an intracardiac suture operation comprising:

a rod provided with a grip member at a proximal end thereof and having a flexible end portion at a distal end thereof;

a piercing catheter having a lumen for movably holding the rod, a flexible distal end portion having a piercing needle at a distal end thereof, and a proximal end portion provided with a hemostatic means at a proximal end thereof;

a sheath having a lumen for movably holding the piercing catheter and provided with a hemostatic means at a proximal end thereof; and an engaging member, i.e., means for engaging an atrial septum, that can be accommodated in the lumen of the piercing catheter and which can be fitted with a suture;

wherein the engaging member when accommodated in the piercing catheter can be pushed out of the piercing catheter by pushing said rod.

The piercing catheter and the sheath are provided at the respective proximal ends thereof with a side injection channel for injecting heparinized physiological saline into the suturing site. The distal end portion of the sheath is bent at a predetermined angle.

DESCRIPTION OF PREFERRED EMBODIMENTS OF THE INVENTION

Preferred embodiments of the invention are described below with reference to the drawings attached hereto.

Referring now to FIGS. 1 to 4, there is shown the device for intracardiac suture according to the present invention comprising:

a rod 3 provided with a grip member 31 at a proximal end thereof and having a flexible end portion;

a piercing catheter 2 having a lumen 21 for movably holding the rod 3 and a flexible distal end portion with a piercing needle 25 at a distal end thereof, and provided with a hemostatic means 24 at a proximal end thereof;

a sheath 1 having a lumen 11 for movably holding the piercing catheter 2 and provided with a hemostatic means 14 at a proximal end thereof; and an engaging member 4 that can be accommodated in the lumen 21 of the piercing catheter 2 and which can be fitted with a suture;

wherein the engaging member 4 when accommodated in the piercing catheter 2 can be pushed out of the piercing catheter 2 by pushing said rod 3.

Figure 3:
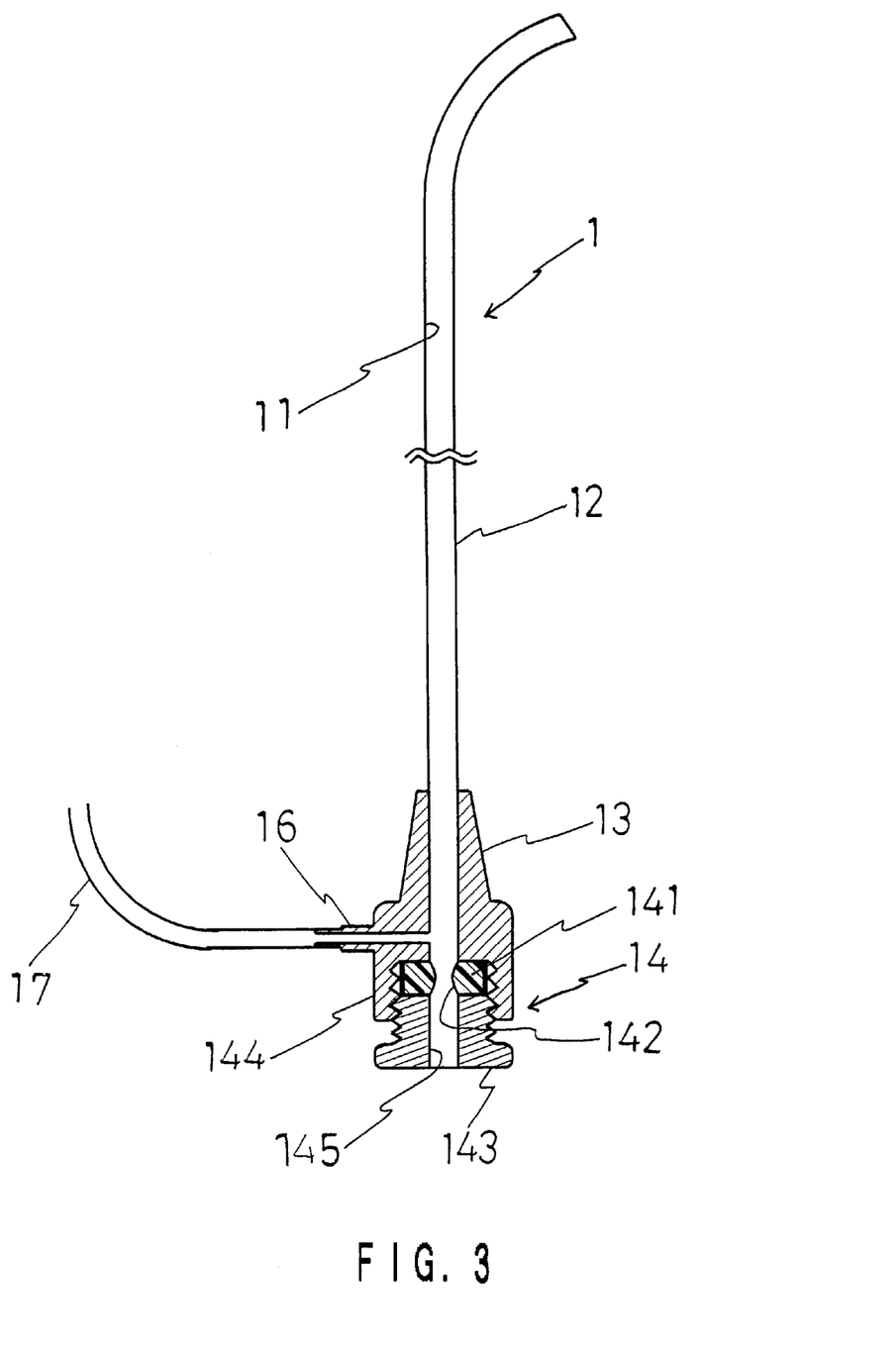
FIG. 3 is a sectional view of the sheath of the device of FIG. 1.

As shown in FIG. 3, the sheath 1 is composed of a sleeve 12 with a lumen 11 for free insertion of the piercing catheter 2. The sleeve 12 is provided at its proximal end with a connector 13. The connector 13 has an inlet of the lumen 11, i.e., an insertion hole 145 for the piercing catheter 2, and is provided with a hemostatic means (or a hemostatic valve) 14 to prevent leakage of the blood during surgical operation. The hemostatic valve 14 is not limited in construction. For example, as shown in FIG. 3, the hemostatic valve 14 is composed of a screw-hole or nut-like means 144 provided in the rear end of the connector 13, and a packing 141 with a central through-hole 142, and a bolt-like member 143 engaged with the screw-hole 144. By driving the bolt-like member 143 into the screwhole 144, the packing 141 is pressed against the bottom wall of the screw-hole 144 to adjust the inner diameter of the through-hole 142. Further, the connector 13 is generally provided with a side injection channel 16 for injecting heparinized physiological saline into the suturing site to prevent occurrence of blood coagulation during a surgical operation. The side injection channel 16 is connected to a side injection tube 17. Preferably, the distal portion of the sleeve 12 is made bendable in correspondence with the bending of the piercing catheter 2.

As the material for the sleeve 12 of the sheath 1, there may be used synthetic resins such as fluororesins (e.g., polytetrafluoroethylene), polypropylene, polyethylene, polyamide, polyethylene terephthalate, polyurethane and the like, and also meshed or coiled stainless steel (e.g., SUS 304). The connector 13 is generally made from a synthetic resin that includes polypropylene, ABS (acrylonitrile-butadiene-styrene) resins, polyvinyl chloride, polyethylene, polyethylene terephthalate and the like, or even from a metal such as stainless steel, brass or the like. The packing 141 of the hemostatic valve 14 may be made from a material with rubber elasticity, for example, synthetic rubber, such as silicone rubber or isoprene rubber, or natural rubber. As the material for the bolt-like means, there may be used synthetic resins such as polycarbonate, ABS resin and the like.

Figure 4:
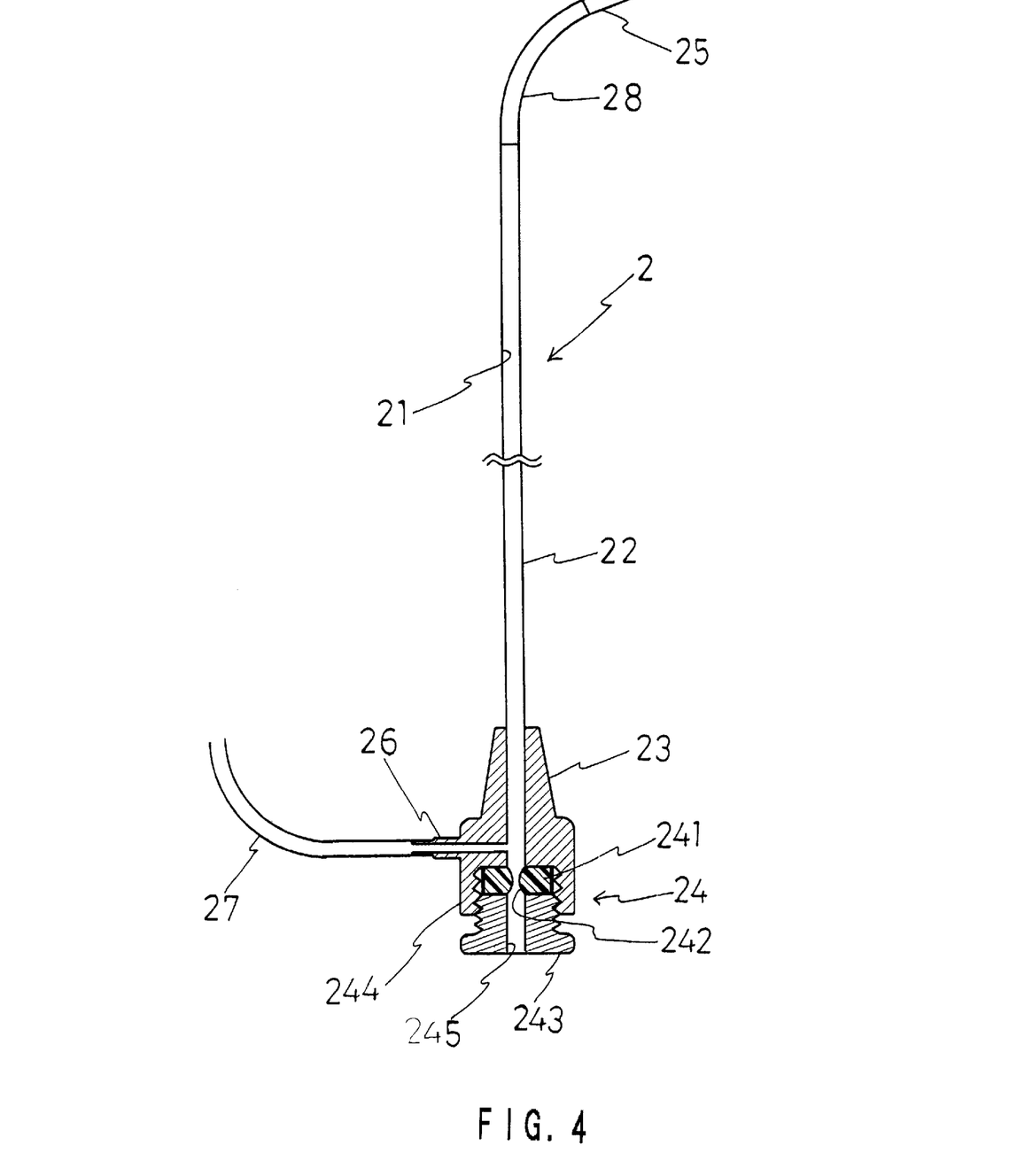
FIG. 4 is a sectional view of the piercing catheter of the device of FIG. 1.
Figure 5:
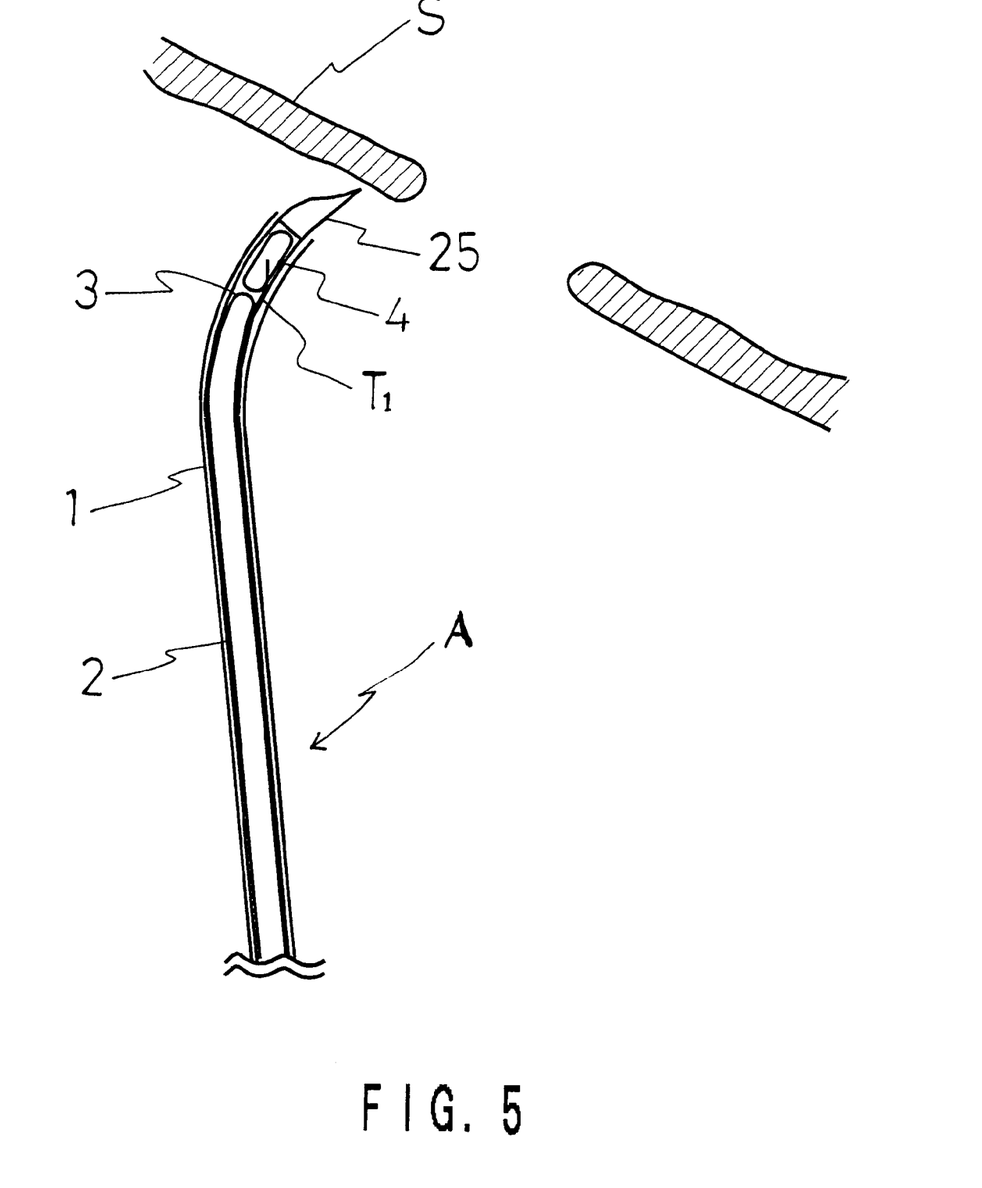
FIGS. 5 to 10 is are explanatory views illustrating an intracardiac suture with the device of the invention.

As shown in FIG. 4, the piercing catheter 2 is composed of a sleeve 22 having a lumen 21 for movably holding the rod 3 and provided at a distal end with a piercing needle 25 and at a proximal end with a connector 23. The connector 23 has an inlet of the lumen 21, i.e., a insertion hole 245 for the rod 3, and is provided with a hemostatic means (or a hemostatic valve) 24 to prevent leakage of blood during surgical operation. The hemostatic valve 24 has the same structure as that of the hemostatic valve 14 of the sheath 1, and is composed of a packing 241, a through-hole 242, a bolt-like member 243 and a nut member 244, as shown in FIG. 4. Further, the connector 23 is generally provided with a side injection channel 26 for injecting heparinized physiological saline into the suturing site to prevent coagulation of the blood during a surgical operation. The side injection channel 26 is connected to a side injection tube 27.

Figure 6:
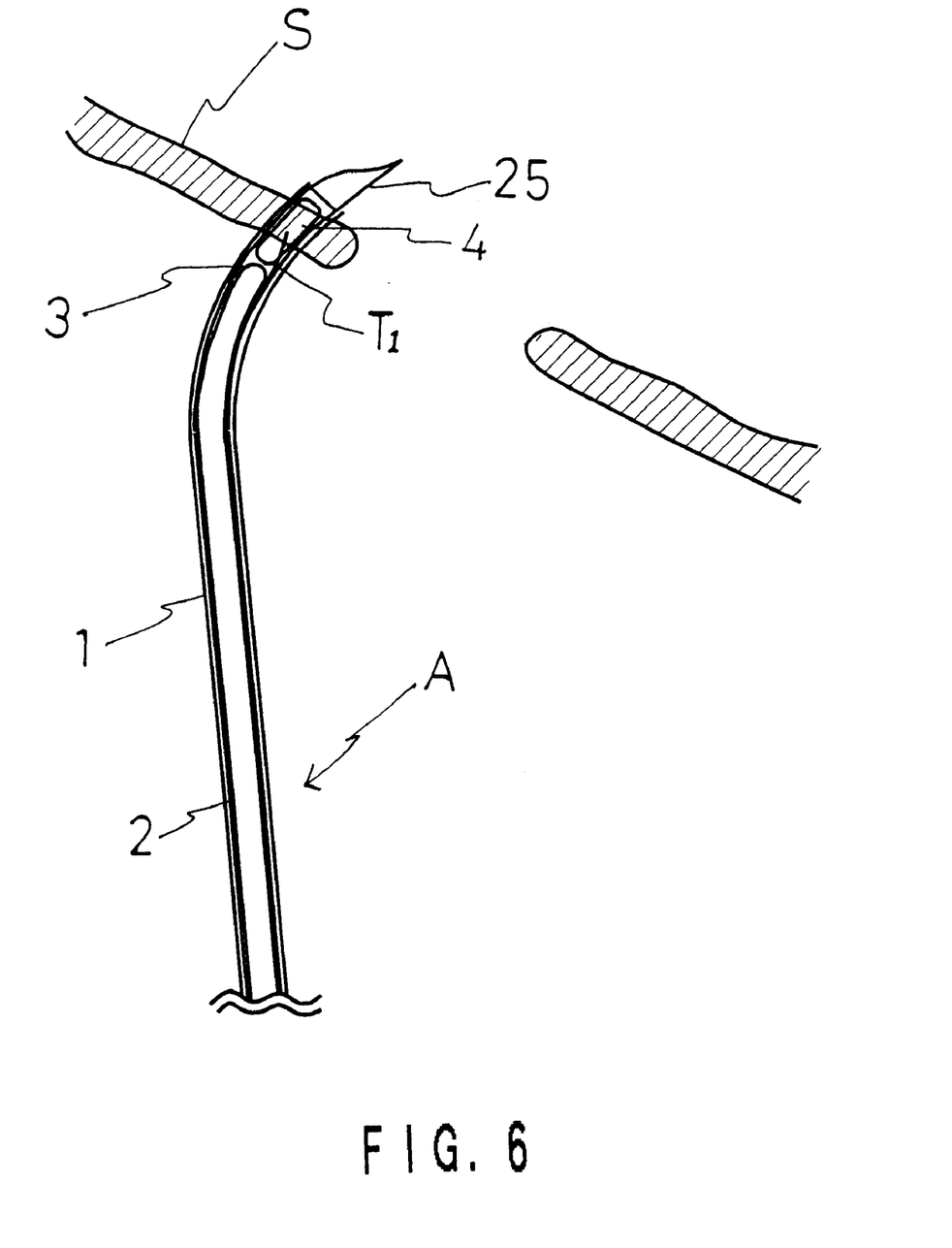

The distal portion 28 of the piercing catheter 2 adjacent to the piercing needle 25 is easily bendable. Preferably, as shown in FIG. 4, the distal portion 28 is bent in correspondence with the shape of the distal portion 11 of the sheath 1. When the piercing catheter 2 is slid forward in the lumen 11 of the sheath 1 and when the top of connector 23 of the piercing catheter 2 is brought into contact with the bottom of the connector 13 of the sheath 1, then a predetermined length of the piercing needle 25 is exposed from the end of the sheath 1, as shown in FIG. 6. The length of the piercing needle 25 exposed is preferably such that the edge of the piercing needle 25 is fully exposed.

Regarding the material of the piercing catheter 2, the sleeve 22 is preferably made of meshed or coiled stainless steel, while the connector 23 is generally made from a synthetic resin such as polypropylene, ABS resin, polyvinyl chloride, polyethylene and polyethylene terephthalate, or a metal such as stainless steel, brass or the like. Preferably, the bendable distal portion 28 may be made from a synthetic resin such as nylon, polyethylene, polyethylene terephthalate or the like, or a meshed or coiled stainless steel. The piercing needle 25 may generally be made of stainless steel such as SUS 304 or the like.

The rod 3 is a long member, provided with a shaft 31 at a proximal end and at a distal end portion 32 being flexible. The length of the rod 3 is such that, when the rod 3 is slid forward in the piercing catheter 2 and when the top of the grip member 31 is brought into contact with the bottom of the connector 23 of the piercing catheter 2, then the engaging member 4 accommodated in the lumen 21 of the piercing catheter 2 is pushed out of the piercing needle 25 of the piercing catheter 2. The rod 3 is typically made from meshed or coiled stainless steel, or a synthetic resin such as polypropylene, polyethylene, polyester, polyethylene terephthalate or the like.

Using the device of the invention, the piercing needle 25 is pierced through an atrial septum and the engaging member 4 is pushed to the opposite side of the atrial septum. Then, the engaging member 4 is released from the device and is positioned on the opposite side of the suture thread "T" (fixed to the engaging member 4) via the atrial septum. Then, by pulling the suture thread "T", the engaging member 4 is engaged with the wall of the atrial septum. To enable the engaging member 4 to be pulled by the suture thread, for example, a small hole (not shown is formed in the center of the engaging member 4, through which the suture thread "T" can be fitted to the engaging member 4. For example, the engaging member 4 is made from the same material as the suture thread "T", and the suture thread "T" is hot-sealed with the engaging member 4. The shape or form of the engaging member 4 is not specifically limited in so far as it can be securely engaged with the wall of an atrial septum. For example, the engaging member 4 can be in any form of a tabular or bead-like form, or in any other form.

Regarding the materials for the engaging member and the suture thread, the engaging member may be made from any of a metal, ceramic, synthetic resin, and the like, and the suture thread may be made from any of silk, polyamide, polypropylene and the like.

Using the thus-constructed device for intracardiac suture according to the present invention, ASD atrioseptopexy is carried out in the following manner. The atrioseptopexy is explained below, with reference to FIGS. 5 to 10.

Figure 1:
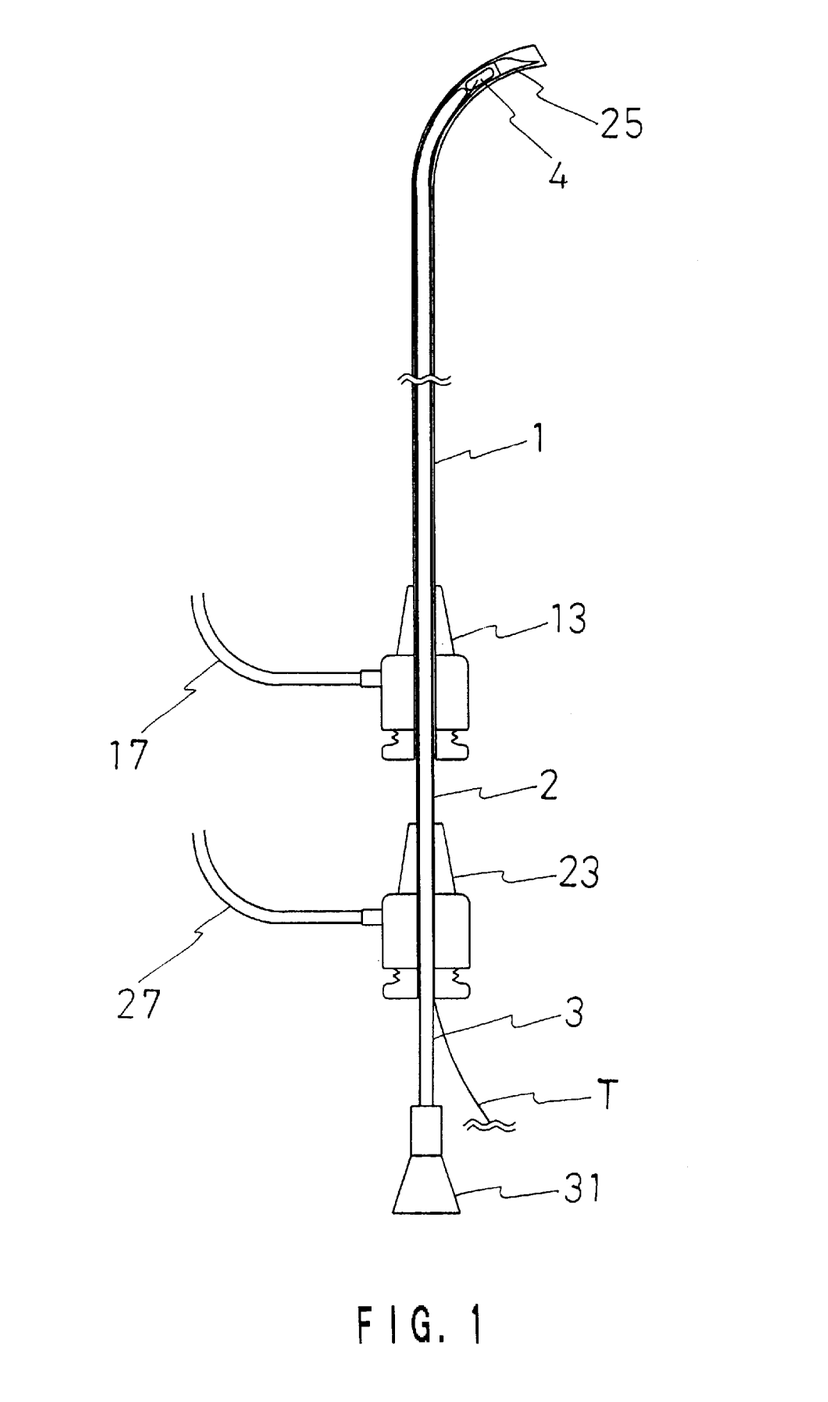
FIG. 1 is a schematic view of a device for intracardiac suture according to the present invention.
Figure 2:
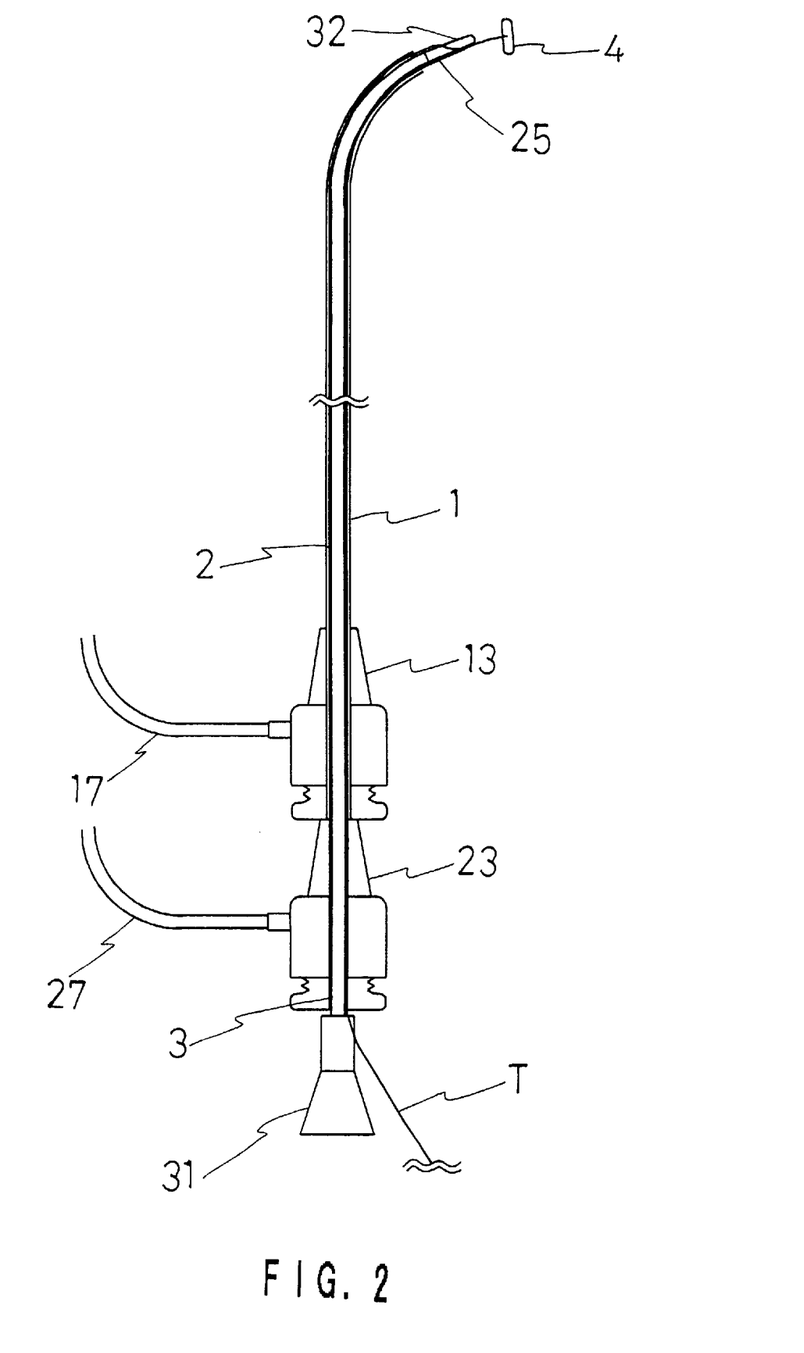
FIG. 2 shows the device of FIG. 1, in which the engaging member has been pushed out from the top of device.

Firstly, the catheter assembly "A" comprises sheath 1, piercing catheter 2, rod 3 and engaging member 4 and both the top of the sheath 1 and the top of piercing needle 25 of the piercing catheter 2 are in the same position, as shown in FIG. 1. The catheter assembly is maneuvered into a sheath (not shown), which has been previously maneuvered into the right atrium of a patient's heart through the femoral vein of the right leg, and is introduced into the right atrium of the patient's heart. After the distal end portion of the catheter assembly "A" has been introduced into the right atrium, the piercing needle 25 is pushed out of the tip of the sheath 1, by pushing the connector 23 of the piercing catheter 2 forward by one hand, while holding the sheath 1 by the other hand, as in FIG. 5. Next, the catheter assembly "A" is pushed to puncture the interatrial septum "S" with the piercing needle 25, whereby the distal end portion of the assembly "A" is introduced into the left atrium, as in FIG. 6. Next, the engaging member 4 is pushed out of the piercing needle 25 of the distal end of the piercing catheter 2 by pushing the rod 3 forward by one hand, while holding the sheath 1 by the other hand as in FIG. 7. Thus, the suture thread "T" in the right atrium is fixed in the atrial septum "S" by means of the engaging member 4 functioning as an anchor in the left atrium.

Figure 7:
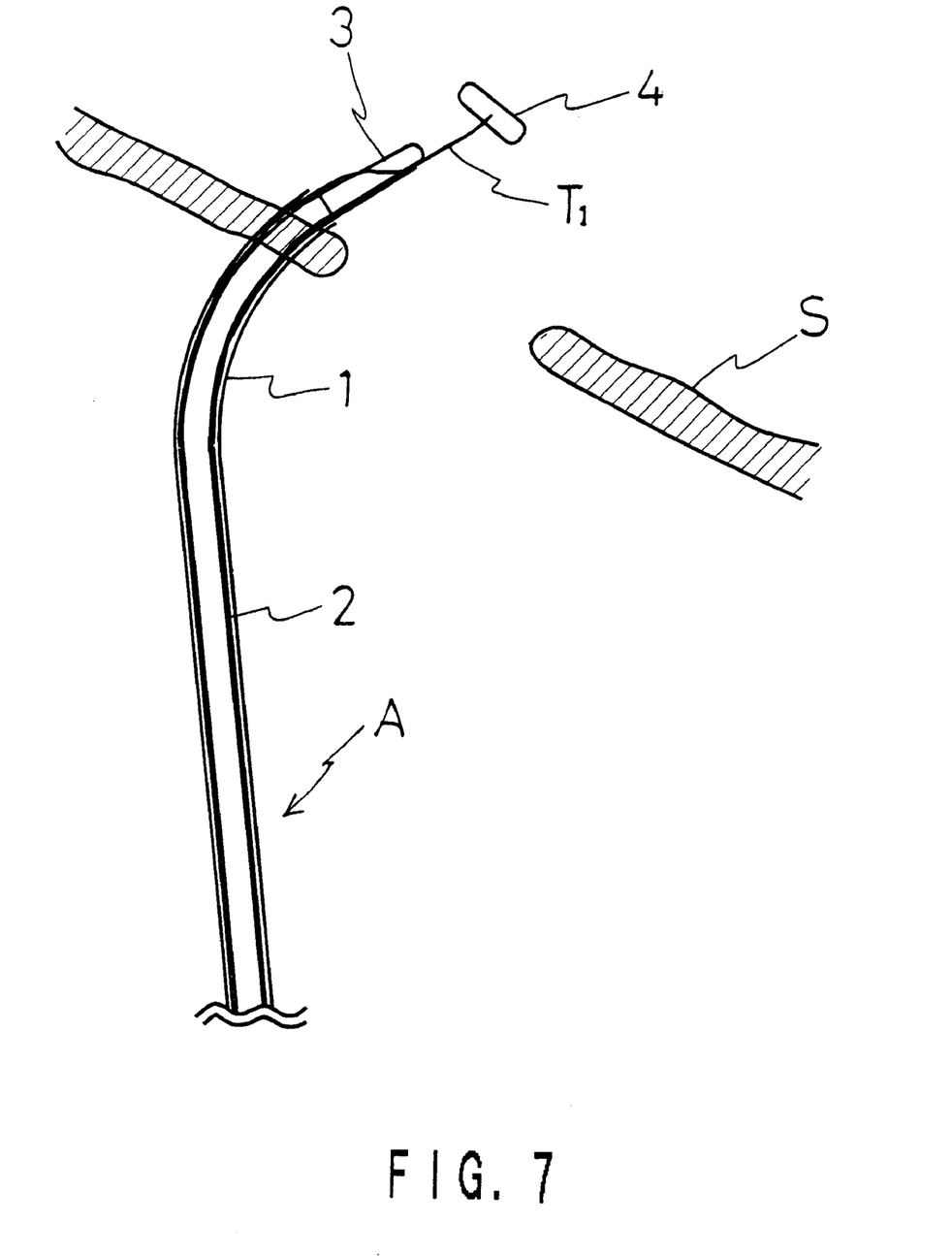

Next, the piercing needle 25 is accommodated in the sheath 1 by pushing the piercing catheter 2, and the catheter assembly "A" is taken out of the body.

Figure 8:
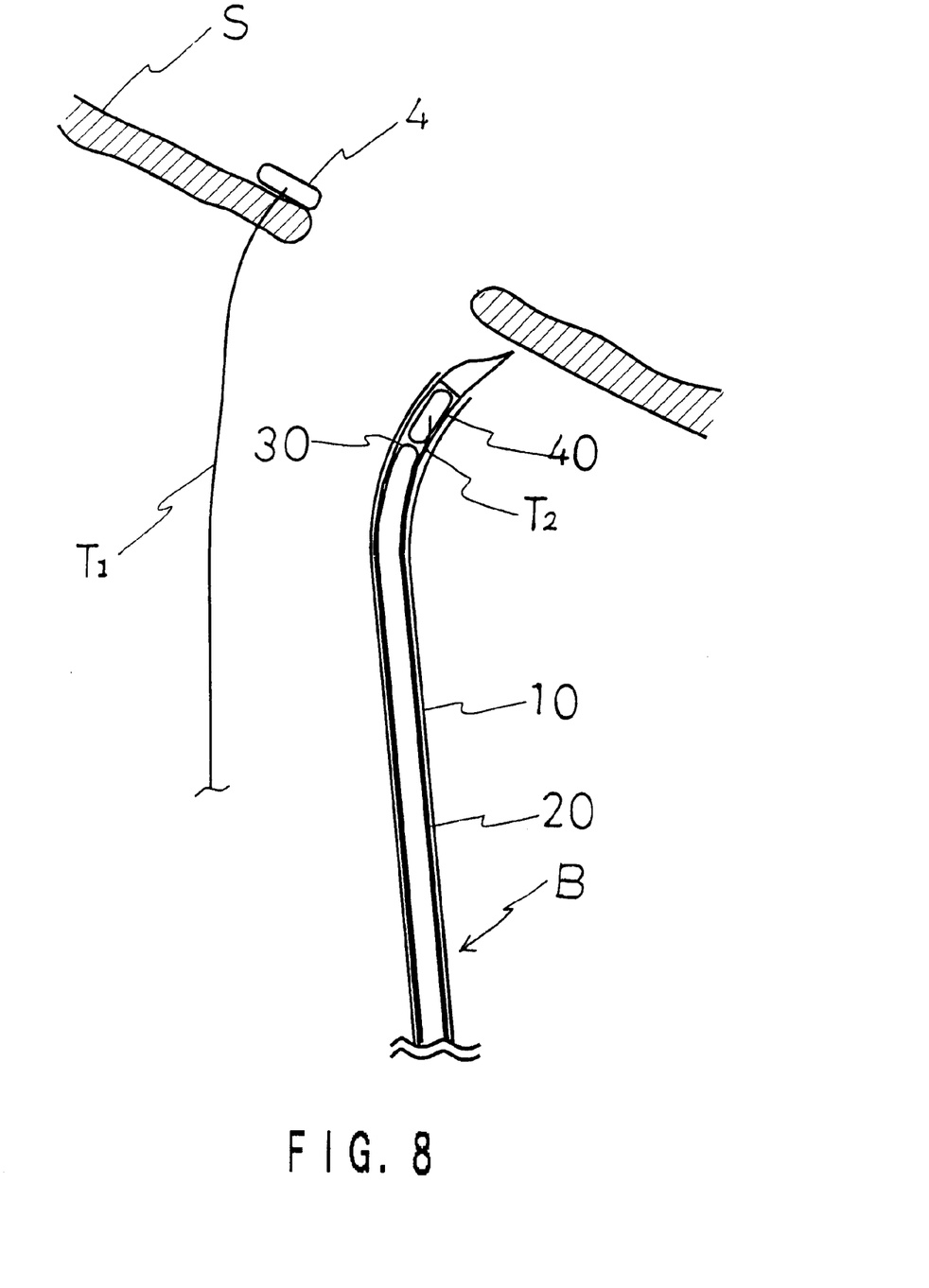
Figure 9:
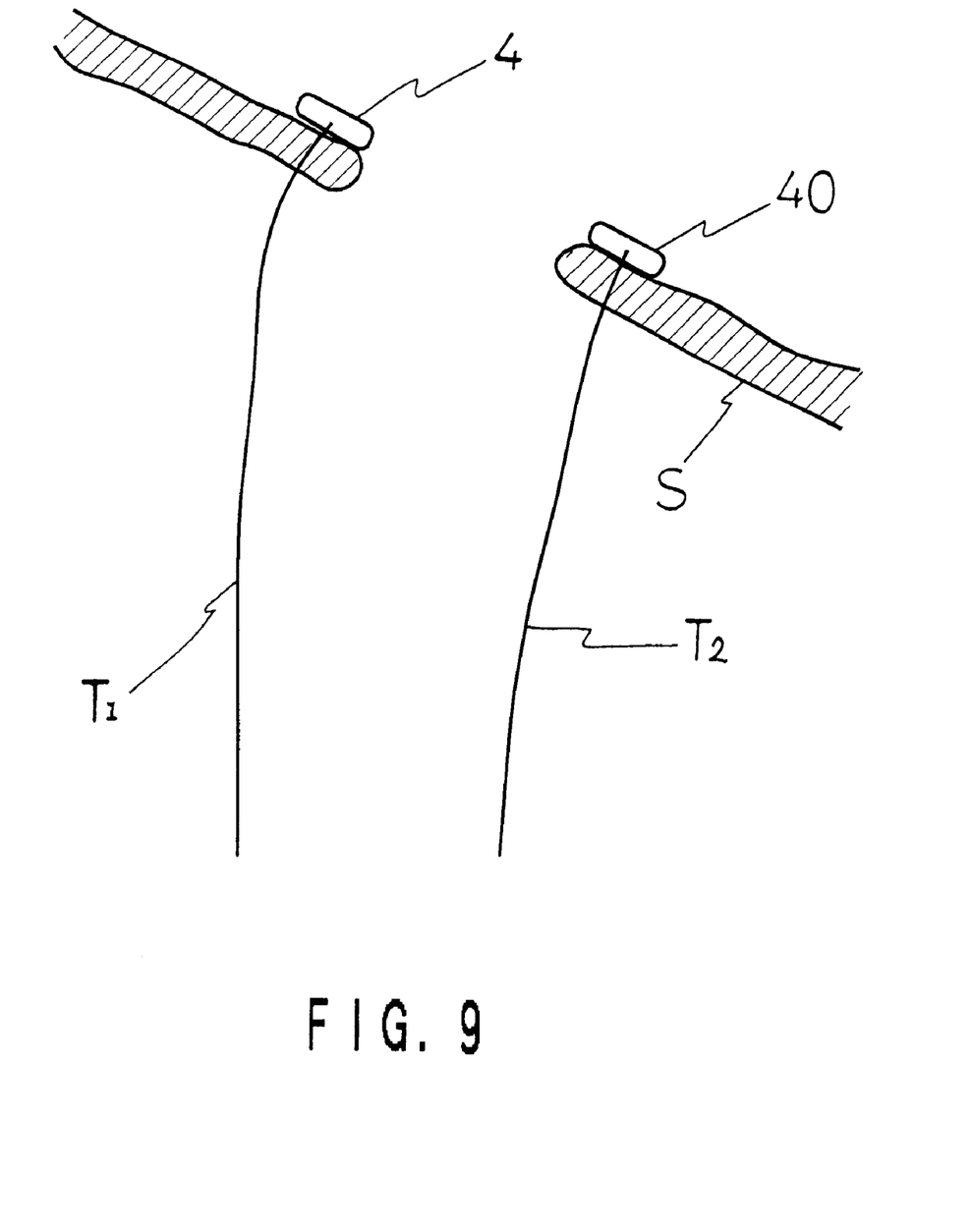
Figure 10:
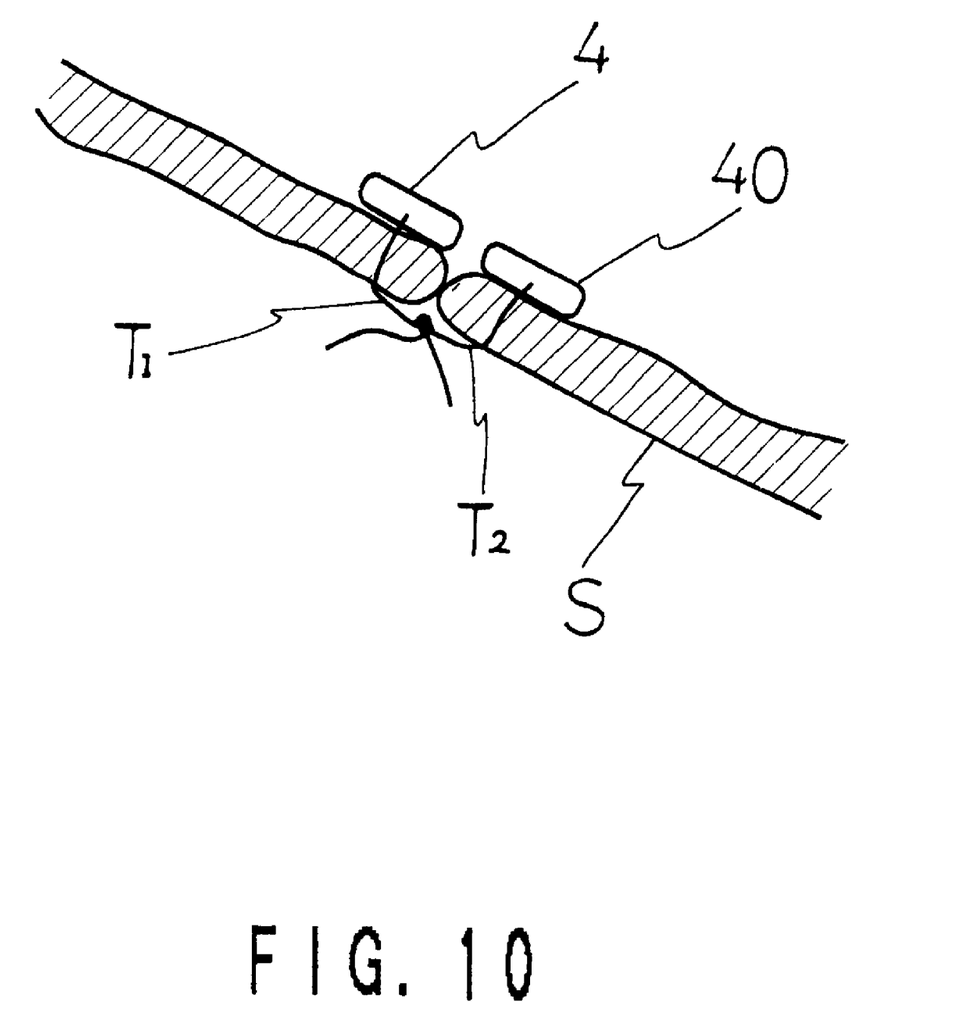

Next, another catheter assembly "B" which is the same as the catheter assembly "A" and which comprises sheath 10, piercing catheter 20, the rod 30 and engaging member 40, is introduced into the right atrium, using the same sheath as that used for introducing the assembly "A" into the right atrium, as shown in FIG. 8. After the catheter assembly "B" has been introduced into the right atrium, the engaging member 40 is pushed out into the left atrium and the suture thread "T2" is fixed in the atrial septum "S", in the same manner as that for the catheter assembly "A", as shown in FIG. 9. Next, the assembly "B" is taken out of the body also in the same manner as that for the catheter assembly "A", and the suture threads "T1" and "T2" are ligated together, using a suture-ligating device (not shown), and the unnecessary parts of the threads are cut off. In this manner, the ASD atrioseptopexy is finished, as in FIG. 10. In case of two or more stitches being required, the same process as above is repeated.

As mentioned above, use of the device for intracardiac suture of the present invention makes it possible to close the affected part by direct suture, so that it can be applied to any form of atrial septal defect. Further, it is possible to close the atrial septal defect completely. Intracardiac suture by the device of the present invention is safe, because the suture leaves smaller foreign substances in the heart than the foreign substances left by using the conventional ASD device of the occlusion plug type.

Although the present invention has been fully described in connection with preferred embodiments thereof with reference to the accompanying drawings, it is noted that various changes and modifications will be apparent to those skilled in the art. Such changes and modifications are to be understood as being included within the scope of the invention as defined by the appended claims.

What is claimed is:

1. A device for intracardiac suture, comprising:

a rod having a proximal end and a distal end and provided with a grip member at the proximal end thereof and having a flexible end portion at the distal end thereof;

a piercing catheter having a lumen for movably holding the rod, a flexible distal end portion having a piercing needle at a distal end thereof, and a proximal end portion provided with a hemostatic means at a proximal end thereof;

a flexible sheath having a lumen for movably holding the piercing catheter, a proximal end and a distal end and provided with a hemostatic means at the proximal end thereof; and a means for engaging an atrial septum and which can be accommodated in the lumen of the piercing catheter and having a suture fitted thereto;

wherein the means for engaging accommodated in the piercing catheter can be pushed out of the piercing catheter by pushing said rod.

2. The device for intracardiac suture according to in claim 1, wherein the piercing catheter and the sheath are provided at the respective proximal ends thereof with a side injection channel for injecting heparinized physiological saline into the suturing site.

3. The device for intracardiac suture according to in claim 1, wherein the distal end portion of the sheath is bent at a predetermined angle.

4. The device for intracardiac suture according to in claim 2, wherein the distal end portion of the sheath is bent at a predetermined angle.

* * * * *